US011015434B2

(12) United States Patent
Molla et al.

(10) Patent No.: US 11,015,434 B2
(45) Date of Patent: May 25, 2021

(54) MICROFLUIDIC DETERMINATION OF WAX APPEARANCE TEMPERATURE

(71) Applicant: SCHLUMBERGER TECHNOLOGY CORPORATION, Sugar Land, TX (US)

(72) Inventors: Shahnawaz Molla, Watertown, MA (US); Abdel Kharrat, Edmonton (CA); Farshid Mostowfi, Boston, MA (US)

(73) Assignee: Schlumberger Technology Corporation, Sugar Land, TX (US)

(*) Notice: Subject to any disclaimer, the term of this patent is extended or adjusted under 35 U.S.C. 154(b) by 451 days.

(21) Appl. No.: 15/022,871

(22) PCT Filed: Sep. 20, 2013

(86) PCT No.: PCT/US2013/060888
§ 371 (c)(1),
(2) Date: Mar. 17, 2016

(87) PCT Pub. No.: WO2015/041672
PCT Pub. Date: Mar. 26, 2015

(65) Prior Publication Data
US 2016/0208601 A1 Jul. 21, 2016

(51) Int. Cl.
G01K 13/00 (2006.01)
E21B 47/07 (2012.01)
(Continued)

(52) U.S. Cl.
CPC .............. *E21B 47/07* (2020.05); *E21B 37/00* (2013.01); *G01N 33/28* (2013.01); *G01N 33/2811* (2013.01); *E21B 49/0875* (2020.05)

(58) Field of Classification Search
None
See application file for complete search history.

(56) References Cited

U.S. PATENT DOCUMENTS 4,023,397 A    5/1977   Ouvrard
5,454,257 A * 10/1995   Per ..................... G01N 33/2835
                                                                                                        374/16
(Continued)

FOREIGN PATENT DOCUMENTS

WO    WO2011014202 A1    2/2011

OTHER PUBLICATIONS

Hammami, A. et al., "Paraffin Deposition from Crude Oils: Comparison of Laboratory Results with Field Data", SPE 54021, Society of Petroleum Engineers, 1999, 4(1), pp. 9-18.
(Continued)

*Primary Examiner* — Lisa M Caputo
*Assistant Examiner* — Nasir U. Ahmed
(74) *Attorney, Agent, or Firm* — Trevor G. Grove

(57) ABSTRACT

A method and system are provided for detecting the wax appearance temperature (WAT) of a hydrocarbon fluid sample. The hydrocarbon fluid sample is run through a microfluidic channel at controlled temperatures while sensing the pressure drop across the channel. The WAT is determined by finding a temperature at which the pressure (drop) across the microfluidic channel caused by a temperature reduction of the hydrocarbon fluid sample does not stabilize over a given time interval, thereby establishing the WAT as being at that temperature or between that temperature and a previous higher temperature where the pressure (drop) stabilized over time.

21 Claims, 4 Drawing Sheets

(51) Int. Cl.
*G01N 33/28* (2006.01)
*E21B 37/00* (2006.01)
*E21B 49/08* (2006.01)

(56) References Cited

U.S. PATENT DOCUMENTS

| | | | |
|---|---|---|---|
| 5,891,262 | A | 4/1999 | Khalil et al. |
| 6,035,706 | A * | 3/2000 | Campagnolo ...... G01N 33/2811 374/23 |
| 6,841,779 | B1 * | 1/2005 | Roehner ............ G01N 33/2811 250/339.06 |
| 7,688,071 | B2 | 3/2010 | Cheng et al. |
| 2006/0008382 | A1 * | 1/2006 | Salamitou ......... B01L 3/502715 422/400 |
| 2009/0066330 | A1 | 3/2009 | Cheng et al. |
| 2010/0174124 | A1 * | 7/2010 | Tonkovich ........... B01J 19/0093 585/23 |
| 2010/0300486 | A1 * | 12/2010 | Hoffman ............... F28G 13/005 134/8 |
| 2011/0288788 | A1 * | 11/2011 | Oh .................... G01N 21/3577 702/25 |

OTHER PUBLICATIONS

Robertson, C. A. et al., "Practical Application of Flow Assurance and Production Chemistry Test Results", SPE 127334, Society of Petroleum Engineers, presented at the SPE Oil and Gas India Conference and Exhibition, Mumbai, India, 2010, 16 pages.

Venkatesan, R. et al., "Wax Deposition During Production Operations: SOTA", OTC 18798, presented at the 2007 Offshore Technology Conference held in Houston, Texas, USA, 2007, 5 pages.
Thanh, N. X. et al., "Waxes and Asphaltenes in Crude Oils", Organic Geochemistry, 1999, 30(2-3), pp. 119-132.
Karan, K. et al., "Measurement of Waxy Crude Properties Using Novel Laboratory Techniques", SPE-62945, presented at the SPE Annual Technical Conference and Exhibition, Dallas, Texas, USA, Society of Petroleum Engineers, 2000, 12 pages.
Pedersen, K. S. et al., "Effect of Precipitated Wax on Viscosity—A Model for Predicting Non-Newtonian Viscosity of Crude Oils", Energy Fuels, 2000,14(1), pp. 43-51.
Monger-Mcclure, T. G. et al., "Comparisons of Cloud Point Measurement and Paraffin Prediction Methods", SPE-54519, Society of Petroleum Engineers, SPE Production and Facilities, 1999, 14(1), pp. 4-16.
Pedersen, K. S. et al., "Phase Behavior of Petroleum Reservoir Fluids", in Phase Behavior of Petroleum Reservoir Fluids, CRC Press: 2007; pp. 199-205.
Hammami, A.; et al., "Cloud Ppoints: Can We Measure or Model Them?", Petroleum Science and Technology, 2003, 21(3-4), pp. 345-358.
Coutinho J. A. P. et al, "The Limitations of the Cloud Point Measurement Techniques and the Influence of the Oil Composition on its Detection", Petroleum Science and Technology, 2005, 23(9-10), pp. 1113-1128.
White, F. M., "Viscous Fluid Flow" in Viscous Fluid Flow, Third ed.; McGraw Hill New York, 2005, 23 pages.
Search Report and Opinion of European Patent Application No. 13893738.8 dated May 10, 2017, 6 pages.

* cited by examiner

MICROFLUIDIC DETERMINATION OF WAX APPEARANCE TEMPERATURE

BACKGROUND

Field

The present application relates to methods and systems for determining the wax appearance temperature of a hydrocarbon fluid sample such as crude oil or gas condensate containing wax dissolved in the liquid phase of the sample. The methods and apparatus of the present application may be conducted and located downhole in a formation or at the Earth's surface at a wellsite or in a laboratory.

Related Art

Hydrocarbon fluids commonly contain paraffin waxes dissolved in the liquid phase. When such fluids are transported from the reservoir to surface facilities decreasing temperature and variations in pressure may cause wax molecules to precipitate out of the liquid phase and deposit as solids on internal surfaces of pipe and other equipment, which is detrimental to production. The deposited layer can reduce the cross-sectional area of a pipeline and impair liquid flow. The problem can be particularly severe in deepwater (temperature≈4° C.) production and transportation since remediation in deepwater environments is both time-consuming and very expensive. From a flow assurance perspective, therefore, it is important to be able to predict the conditions which are (un)favorable for wax formation.

Paraffin waxes are essentially mixtures of long-chain hydrocarbons (n-paraffins) with carbon chain lengths ranging from $C_{17}$ to $C_{90+}$ which are crystalline in nature. As the temperature of the oil drops, the solubility of the high molecular weight paraffins in the liquid decreases and dissolved wax molecules tend to crystallize below a certain temperature. The highest temperature at which the crystallization starts at a given pressure is commonly referred to as the wax appearance temperature (WAT) although the terms "wax precipitation temperature" (WPT) and "cloud point" (CP) have also been used to describe the phenomenon. Wax appearance temperature is primarily influenced by the composition of a hydrocarbon fluid (wax content and the distribution of paraffin molecules) and thermal history (e.g., temperature/cooling rate). Wax content of a hydrocarbon fluid is a measure of the total wax-forming components in the fluid. The solid fraction appearing at WAT consists of a distribution of long chain paraffins and with further decreases in temperature, paraffins of shorter chain lengths begin to crystallize and increase the solid fraction.

As shown in FIG. 1, when wax-containing hydrocarbon fluids are cooled below their WAT, the size and quantity of wax crystals increases as precipitation continues. If left undisturbed, these crystals begin to develop an interlocking network that gives the fluid a gel-like structure. Hydrocarbon fluid becomes trapped in the porous structure and the effective viscosity of the system increases significantly. Depending on the amount of wax and the gel strength, the hydrocarbon fluid may cease to flow at a certain temperature. The lowest temperature at which a fluid ceases to flow is referred to as pour point, a measure of the presence of wax in a hydrocarbon fluid. There are several analytical methods for the quantitative measurement of WAT. Some of the widely used methods are ASTM methods (ASTM D2500, ASTM D3117), cold finger, filter plugging (FP), cross-polar microscopy (CPM), differential scanning calorimetry (DSC), light transmission method, acoustic cavity resonance, and near-infrared spectroscopy (FT-NIR), See, e.g., Karan, K., Ratulowski, J., "Measurement of Waxy Crude Properties Using Novel Laboratory Techniques", *SPE Annual Technical Conference and Exhibition*, Dallas, Tex., Oct. 1-4, 2000; Coutinho, J. A. P., Daridon, J. L., "The limitations of the cloud point measurement techniques and the influence of the oil composition on its detection", *Petroleum Science and Technology* 2005, 23, (9-10), 1113-1128; and U.S. Pat. No. 6,841,779 entitled "Measurement of Wax Precipitation Temperature and Precipitated Solid Weight Percent Versus Temperature by Infrared Spectroscopy".

Alteration of the hydrocarbon fluid viscosity due to wax precipitation has also been explored for detection of WAT in complex viscosity measurements. See, Pedersen, K. S., Ronningsen, H. P., "Effect of precipitated wax on viscosity—A model for predicting non-Newtonian viscosity of crude oils", *Energy & Fuels* 2000, 14, (1), 43-51. Wax appearance temperature in oil was also measured by measuring the change in sample volume as a function temperature in a pressurized cell. See U.S. Pat. No. 5,454,257 entitled "Method of Determining Wax Appearance Point of a Complex Real Fluid Crude Liquid Petroleum Composition and of Determining Quantity of Wax Precipitated Therefrom." However, the detection of volume change following wax precipitation is highly dependent on the amount of wax present in the sample. In U.S. Pat. No. 6,035,706, entitled "Method and Apparatus for Determining the Wax Appearance Temperature of Paraffinic Petroleum Oils", measurement of density of petroleum fluids as a function of temperature is used to detect wax appearance and to measure wax content. Due to crystallization kinetics, the measurement method can have an impact on the measured WAT and the value should generally be verified by using two different techniques.

Experimentally measured WAT depends on the sensitivity of the instrument in each specific method. ASTM methods require visual inspection of a sample volume in a cell with a long path length and do not work well with dark oils. With the filter plugging method, the increase in pressure drop is measured across a filter while the precipitated wax is collected on the filter in a temperature controlled flow loop. Although the method is simple to implement, detection is limited by the amount of wax in the crude oil. A solid detection system (SDS) uses the light transmission method where the power of transmitted light through the oil sample (both live and stock tank oil) is measured to detect the appearance of wax crystals. In U.S. Pat. No. 7,688,071, entitled "NMR Measurement of Wax Appearance in Fluids", a low field nuclear magnetic resonance (NMR) technique is used for solids detection and WAT measurement. Compared to other methods, the CPM and DSC methods have been found to provide more accurate values of WAT when the sample volume is small. Both methods can measure WAT of live oils in a high pressure cell. Due to the higher sensitivity of the detection method (a minimum wax crystal size in the order of 2 microns) the CPM method provides the most sensitive WAT measurement for any sample and shows good agreement with field data. See, e.g., Monger-McClure, T. G., et al., "Comparisons of cloud point measurement and paraffin prediction methods", *SPE Production and Facilities* 1999, 14, (1), 4-16. However, since CPM is a visual technique the measured WAT is highly operator-dependent.

Accurate measurement methods, such as CPM and DSC are confined to laboratory environments where the sophisticated instruments used must undergo frequent calibration and regular maintenance to ensure the accuracy of measurements. Even with highly sophisticated laboratory equipment such as CPM, if sample quality is not high, issues such as the presence of emulsified water droplets in the sample can affect wax appearance detection.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method and system is provided that measures wax appearance temperature (WAT) of a liquid sample containing dissolved waxes. The method and system involve detecting changes in pressure drop in a temperature-controlled hydrocarbon fluid sample flowing through a microchannel (i.e., a channel having a hydraulic diameter less than 1 mm).

In one embodiment, a hydrocarbon fluid sample containing dissolved waxes is pumped through a microchannel which is maintained at a first temperature at a constant flow rate, and the pressure difference between an upstream location and downstream location of the channel is monitored and should be relatively constant. The temperature is then reduced to a second temperature and the pressure difference is monitored. If the pressure difference after an initial change continues to increase over a predetermined period of time, a determination is made that the WAT is between the two (first and second) temperatures. However, if the pressure difference after an initial change remains at a relatively constant value for a predetermined period of time, the temperature is again reduced to a lower temperature and the pressure difference is monitored. This cycle is repeated until the pressure shows an indication of continuous increase over the predetermined period of time, thereby signifying that the WAT of the sample is between the temperature where the pressure is increasing and the previous temperature where the pressure remains substantially constant.

In another embodiment, after a determination is made that the WAT of a hydrocarbon fluid sample containing dissolved waxes is between two temperatures, the crude oil sample is pumped through a microchannel at the higher of the two temperatures and the temperature is then reduced to a temperature between the higher and the lower of the two temperatures (i.e., in a finer temperature step) to see whether the pressure difference remains at a relatively constant value for a predetermined period of time after an initial change or whether it continues to increase. The cycle is continued at finer temperature steps until a determination is made that the pressure is continuing to increase after a temperature drop, thereby more specifically establishing the WAT of the sample.

In one embodiment, the pressure difference is taken between the inlet to the microchannel and the outlet of the microchannel.

In one embodiment, the microchannel is embodied in a microfluidic chip or capillary. In one embodiment the microfluidic chip or capillary is arranged as a serpentine channel. In another embodiment, the microfluidic chip or capillary is arranged as a straight channel.

DETAILED DESCRIPTION

Figure 1:
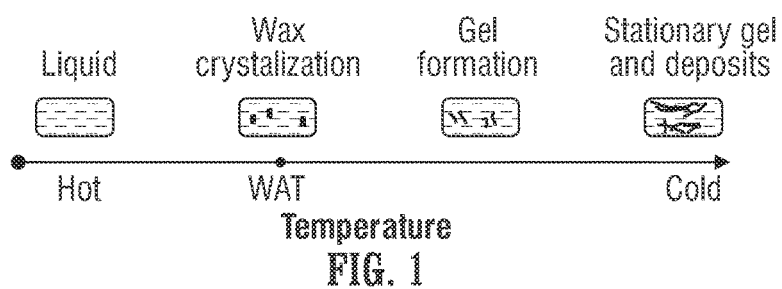
FIG. 1 is a schematic diagram of a wax formation process as a liquid containing wax is cooled to and below its wax appearance temperature.
Figure 2:
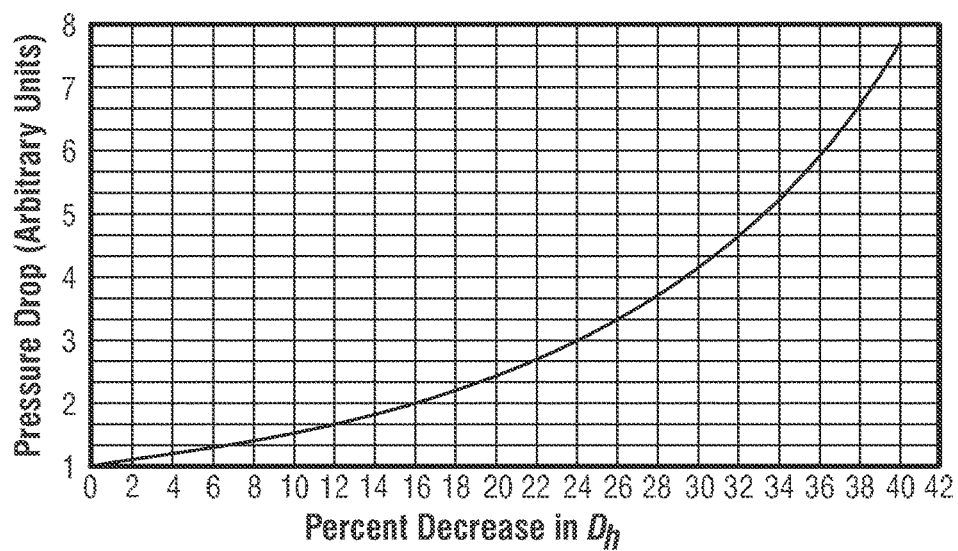
FIG. 2 is a graph showing the effect of a decrease in hydraulic diameter on the pressure drop in a channel.

Before turning to details of systems and methods, a short discussion of the theory of fluid flow that relates to the systems and methods is useful. In particular, the pressure drop across a (micro)channel in which a hydrocarbon fluid is being pumped at a constant flow rate may be defined as the difference in pressure between the inlet and outlet of the channel. In a fully developed laminar flow through a circular channel, the pressure drop necessary for driving the liquid at a specified flow rate can be calculated by using the Hagen-Poiseuille equation:

$$\Delta p = \frac{128\mu_L QL}{\pi D_h^4} \qquad (1)$$

where, $\mu_L$ is the liquid viscosity (which is a function of temperature), Q is the average volumetric flow rate through the channel, L is the total channel length, and $D_h$ (4× cross-sectional area/wetted perimeter) is the hydraulic diameter of the channel. For a constant flow in a fixed-length channel the pressure drop scales linearly with the liquid viscosity. However, the channel diameter has a significantly larger influence (fourth power of $D_h$) on the pressure drop as illustrated in FIG. 2. It should be noted that the surface-to-volume ratio varies as $D_h^{-1}$.

When a hydrocarbon fluid containing wax-forming compounds is injected into a microchannel, the hydrocarbon fluid quickly changes to the temperature of the channel walls due to the small volume of the hydrocarbon fluid relative to the high surface contact area. As long as the temperature of the microchannel is higher than the WAT of the sample, the apparent viscosity of the sample will increase monotonically according to the Newtonian viscosity model. However, when the temperature drops to the WAT, some of the wax will precipitate in the bulk hydrocarbon fluid phase as solid particles and some will deposit on the inner walls of the channel.

Hydrocarbon fluid inside a microchannel is exposed to a considerably larger surface area than would be the case in a large pipe. As a result, the surface area inside a microchannel provides a favorable location for wax crystal deposition and enhances the probability of wax precipitation and deposition at the wall. The parabolic laminar velocity profile also causes particles to migrate due to particle rotation in the shear flow. Wax deposition on the channel wall decreases the effective cross-sectional area of the channel which in turn increases pressure drop and wax particles suspended in the bulk hydrocarbon fluid increase the apparent viscosity of the hydrocarbon fluid. When present in sufficiently high concentrations, the wax particles will change the flow properties of the hydrocarbon fluid/wax suspension from Newtonian to non-Newtonian behavior. See, Pedersen, K. S., Ronningsen, H. P., "Effect of Precipitated Wax on Viscosity—A Model for Predicting Non-Newtonian Viscosity of Crude Oils", *Energy & Fuels* 2000, 14, (1), 43-51, and Pedersen, K. S., Christensen, P. L., "Phase Behavior of Petroleum Reservoir Fluids", *Phase Behavior of Petroleum Reservoir Fluids*, CRC Press (2007) pp. 199-205. If the wax precipitation continues with a further drop in temperature, the pressure drop required to maintain a constant flow will increase exponentially. Therefore, pressure drop in a microchannel due to the appearance of wax particles and consequent blockage of the flow area responds according to changes in temperature.

Figure 3A:
FIG. 3A is a diagram of a short straight microchannel.
Figure 3B:
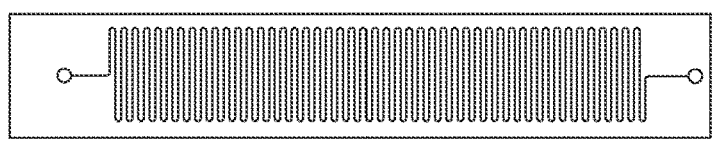
FIG. 3B is a diagram of a long serpentine microchannel.
Figure 3C:
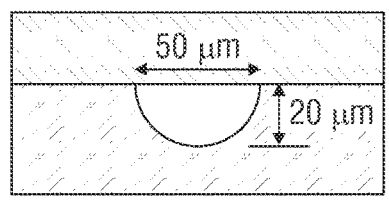
FIG. 3C is a cross-section through the microchannel of FIGS. 3A and 3B.

Turning now to FIGS. 3A and 3B, first and second embodiments of microchannels are shown. FIG. 3A shows a short straight microchannel (e.g., length=80 mm) and FIG. 3B shows a long serpentine microchannel (e.g., length=1.7 m). Both channel configurations may have the same cross-sectional profile; e.g., the cross-sectional profile shown in FIG. 3C. As seen in FIG. 3C, a microfluidic chip is formed from glass plates using microfabrication processes with one plate having a channel with a cross-sectional channel profile that is substantially semicircular (diameter at the top=50 microns, height=20 microns) and the other plate located across the top of the channel. In some embodiments, the microchannel has a length between 80 mm and 1.7 m. In other embodiments, the microchannel has a length greater than 1.7 m or less than 80 mm. In some embodiments, the microchannel has shape that is not straight and not serpentine. In further embodiments, the microchannel has a cross-sectional shape other than substantially semicircular. In some embodiments, the microchannel has a diameter other than 50 microns. In some embodiments, the microchannel has different types of geometric cross-sectional shapes along the length to control flow. In some embodiments, the microchannel has different types of surface roughness on the internal surface of the microchannel.

Figure 4:
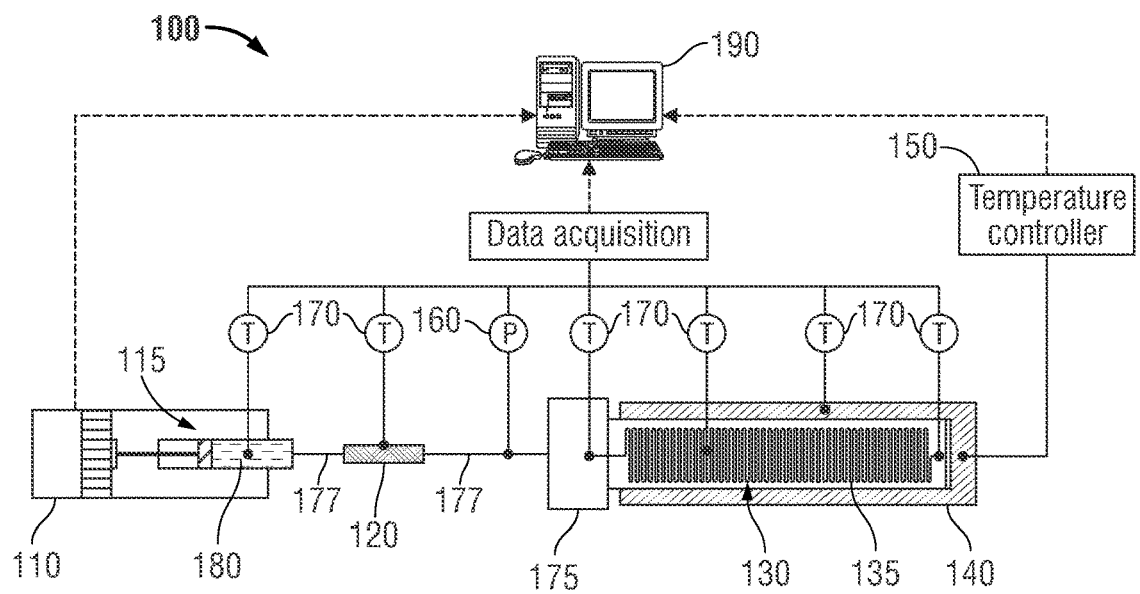
FIG. 4 is a schematic diagram of an embodiment of a system for determining the WAT of a liquid.

As seen in FIG. 4, one embodiment of a system 100 is provided for determining a WAT of a liquid. System 100 includes a precision syringe pump 110, a syringe (injector) 115, a filter 120, a microfluidic chip 130 having a microchannel 135, a temperature control device 140, such as a thermo-electric or Peltier plate, a temperature controller 150, and a pressure sensor 160. Additional elements such as a plurality of temperature sensors 170 coupled to some of the other elements and a chip holder or manifold 175 to facilitate delivery of the fluid sample to the microfluidic chip 130 without leakage are also seen.

In FIG. 4, a hydrocarbon fluid sample 180 is loaded in a heated syringe 115 (such as a Hamilton 1700 series available from Hamilton Company of Reno, Nev., USA) and through the use of the precision syringe pump 110 (such as a neMESYS 1366 available from Cetoni GmbH of Korbussen, Germany) injected into the microchannel 135 of the microfluidic chip 130 via the inline filter 120 (such as a 20 micron filter available from IDEX Corporation of Lake Forest, Ill., USA) which prevents some inorganic solids that could potentially clog the microchannel from entering. The hydrocarbon fluid flows through a flow line or metal tubing 177 from the syringe 115 to the inline filter 120 and from the inline filter 120 to the manifold 175. All components leading to the microchannel 135 are heated with heat tape (such as a Kapton flexible heater available from Omega Engineering of Stamford, Conn., USA) and insulated to maintain a constant temperature. In one embodiment, temperature sensors 170 (such as Omega 5TC-TT-K 40-36, accuracy±0.3° C., thermocouples available from Omega Engineering) are used to monitor the temperature of various parts of the system: e.g., syringe 115, inline filter 120, and microfluidic chip 130.

A pressure sensor 160 (such as an Omega PX409, accuracy±0.4 psi, available from Omega Engineering) is installed in flow line 177 upstream of microfluidic chip 130 to measure the pressure at the inlet of microchannel 135. The outlet at the end of microchannel 135 is open to atmospheric pressure. If necessary for accurate pressure measurement a second pressure sensor may be placed at the outlet of microchannel 135. Microfluidic chip 130 is placed on a temperature-controlled cooling/heating surface (temperature control device) 140 (such as a CP-110 available from TE Technology Inc. of Traverse City, Mich., USA) that is connected to a controller 150 (such as a TEC model TC-36-25 RS485 also available from TE Technology Inc.) thereby enabling temperature control of the microfluidic chip 130 to be carried out independently. Several temperature sensors 170 are used to monitor the temperature gradient on the temperature control device 140, along the microfluidic chip 130, and in the fluid at the exit of the microfluidic chip 130.

In one embodiment data received from thermocouples 170, pressure sensor 160, and syringe pump 110 are provided to a computer or processor 190 for monitoring. Based on the data, and using equation (1), the computer or processor 190 can determine whether the WAT of a hydrocarbon fluid sample has been reached or not (as described in more detail below). If not, the computer or processor 190 can be used via the temperature controller 150 to control the temperature settings of the temperature control device 140.

In another embodiment the data received from the pressure sensor 160 is monitored by a monitor that can provide a visual readout, thereby permitting an operator to adjust temperature control device 140 accordingly.

In one embodiment, the WAT of a hydrocarbon fluid sample is measured using the microfluidic chip 130 by providing the hydrocarbon fluid sample to a syringe 115 which is heated to a temperature that exceeds the WAT of the hydrocarbon fluid sample. By way of example, the hydrocarbon fluid sample 180 in syringe 115 can be heated to a predetermined temperature. By way of example, the predetermined temperature can be 65° C. The hydrocarbon fluid sample 180 is then injected into a microchannel through the filter 120 and flow lines 177. The microchannel can be a microchannel such as the long serpentine microchannel 135 of FIG. 4. It is noted that the initial injection pressure for the hydrocarbon fluid sample at 65° C. depends on the sample viscosity. The flow rate can be adjusted to maintain low pressure while providing the flowing liquid sufficient time in the microchannel to attain the temperature of the microchannel walls. By way of example only, a flow rate of between 0.05 to 0.1 microliters/minute can be used.

With the hydrocarbon fluid sample 180 flowing in the microchannel 135, the pressure drop across the microchannel (i.e., from one end to the other) is monitored by the pressure sensor 160. In one embodiment, the temperature of the microchannel is decreased in steps (e.g., 10° C. steps) as the hydrocarbon fluid flows through the microchannel 135. As is described in more detail below, the measured pressure drop increases with a temperature drop due to an increase in viscosity. However, as long as the hydrocarbon fluid sample is above its WAT, after the temperature drops, the pressure drop will increase but then reach a steady state value. However, if the temperature of the sample decreases below the WAT of the sample, the measured pressure drop rises because of the increase in viscosity, but then continues to rise and does not reach a steady state value due to the effect of wax precipitation causing the effective diameter of the microchannel to continue to decrease. Thus, when the data from the pressure sensor 160 indicates that the pressure drop continues to increase beyond a time period when it is expected that it would have otherwise reached a steady state value, a determination is made that the hydrocarbon fluid sample temperature is below its WAT. By knowing the temperature at that time, and the previous temperature tested, a determination can be made that the WAT of the sample is between those two values.

In one embodiment, once it is determined that the WAT of a hydrocarbon fluid sample is between two values, the hydrocarbon fluid sample may be pumped through a microchannel at or near the higher of the two temperatures. If the same microchannel is used, the increased temperature may cause the wax on the walls of the microchannel to dissolve such that pressure drop decreases. Increased flow rate may also be used to push out the precipitated wax. The temperature of the microchannel may then be reduced to a temperature between the higher and the lower of the two temperatures (i.e., in a finer temperature step such as 1° C. or 2° C.) and the pressure drop monitored to see whether the pressure drop remains at a relatively constant value for a predetermined period of time after an initial change or whether it continues to increase. The cycle is continued with the temperature being decreased in the finer temperature steps until a determination is made that the pressure is continuing to increase after a temperature drop, thereby more specifically establishing the WAT of the sample between the temperatures established by the finer temperature steps.

In another embodiment, once it is determined that the WAT of a hydrocarbon fluid sample is between two values, the hydrocarbon fluid sample may be pumped through a microchannel at a relatively high starting temperature. If the same microchannel is used, the increased temperature may cause the wax on the walls of the microchannel to dissolve such that pressure drop decreases. Increased flow rate may also be used to push out the precipitated wax. The temperature of the microchannel may then be reduced in the same larger temperature steps until the temperature is near the WAT of the hydrocarbon fluid sample. Then, the temperature is controllably reduced in finer temperature steps such as 1° C. or 2° C.) and the pressure drop monitored to see whether the pressure drop remains at a relatively constant value for a predetermined period of time after an initial change or whether it continues to increase. The cycle is continued with the temperature being decreased in the finer temperature steps until a determination is made that the pressure is continuing to increase after a temperature drop, thereby more specifically establishing the WAT of the sample between the temperatures established by the finer temperature steps.

Figure 5:
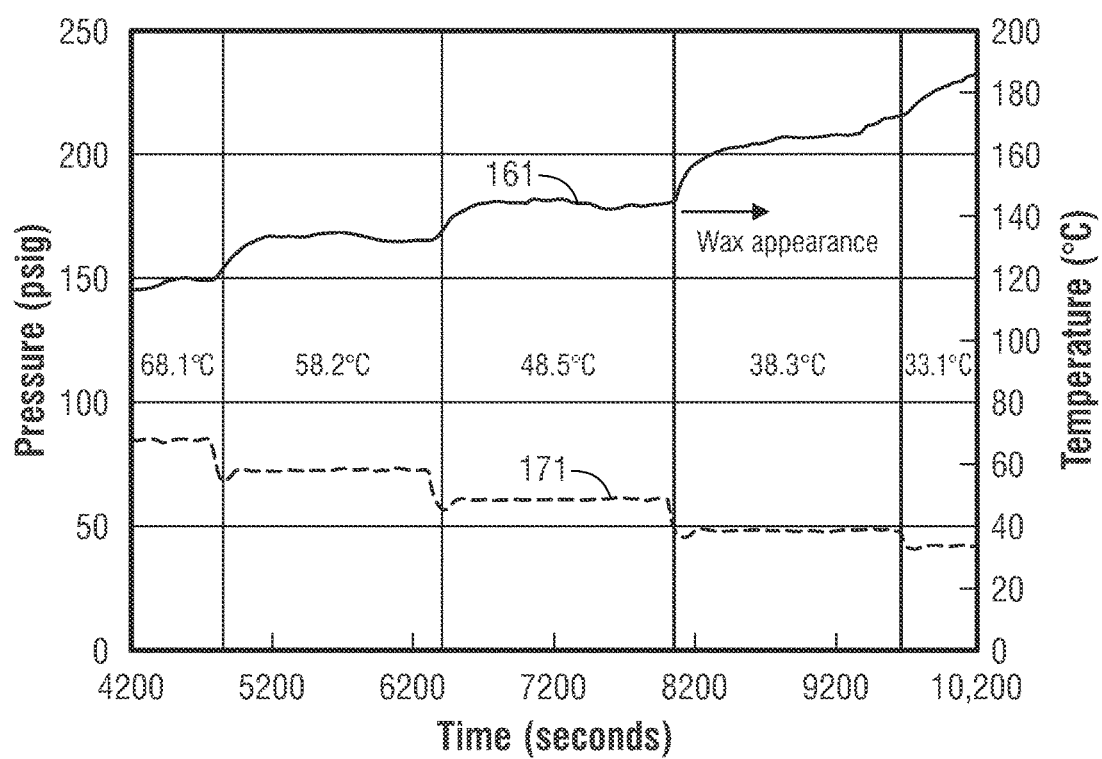
FIG. 5 is a pressure and temperature profile of oil being tested according to one embodiment of a method for determining the WAT of the oil.

FIG. 5 illustrates the pressure and temperature profile recorded during the WAT measurement of a stock tank oil (STO) sample based on the procedure described above with the oil sample flowing through the microchannel serpentine path of FIGS. 3B and 3C at a rate of 0.05 microliters/minute. The pressures and temperatures are plotted on the left and right vertical axes respectively. As indicated in FIG. 5, the temperature 171 was decreased in relatively large steps (approximately 10° C.) from a starting temperature of 68.1° C. over time. After the first and second temperature drops, the pressure 161 (pressure drop across microfluidic chip 130) increased and then plateaued (was stable) with small fluctuations. However, after the temperature of the microchannel 135 was dropped from 48.5 to 38.3° C., the pressure steadily increased. After approximately 25 minutes, the temperature of the microchannel was dropped by an additional 5° C. to confirm wax precipitation, and the slope of the pressure curve 161 further increased due to wax formation in the microchannel 135. This was a clear indication that the wax crystallization started between 48.5° C. and 38.3° C.

Figure 6:
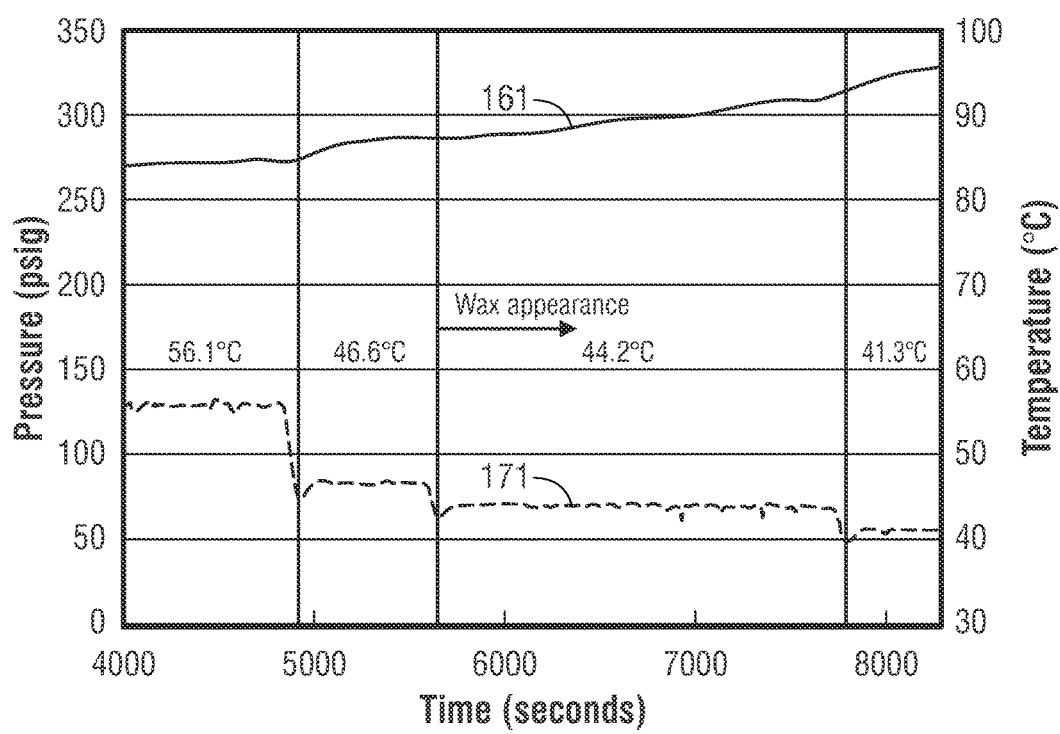
FIG. 6 is a pressure and temperature profile of oil being tested according to a second embodiment of a method for determining the WAT of the oil.

Using the same STO sample now running at 0.08 microliters/minute through the microchannel, and as seen in FIG. 6, the temperature 171 of the microchannel 135 was then increased to 56.1° C. and then reduced in a large step to 46.6° C. (near the 48.5° C. "high" temperature of the WAT range). After the pressure 161 plateaued, the temperature was decreased by about 2° C. to 44.2° C. The recorded pressure then showed a continuous rise for over thirty minutes. The oil temperature was then decreased by about 3° C. more to confirm wax precipitation, and the slope of the pressure curve increased further due to wax formation in the microchannel 135. Based on the pressure variation with temperature, the WAT was determined to be approximately 44° C. for this sample, the highest temperature at which the presence of wax was detected with certainty. The WAT of the same sample was determined to be 46° C. by the CPM technique.

In one aspect, the WAT of several black oils was measured using the microfluidic technique hereinbefore described. Stock tank oil samples were collected by flashing live oils at high temperature (>65° C.) and the WAT of the samples was also measured by CPM. Wax content (by mass) of the samples measured based on the UOP46-64 solvent extraction method ranged from 2.5 to 11.0 percent, excluding Oil A. Measurement data is listed in Table 1.

TABLE 1

STO sample descriptions

| Sample | WAT by CPM (° C.) | WAT by Microfluidic Technique (° C.) | Wax Content (Percent) |
| --- | --- | --- | --- |
| Oil A | 53.4 | 54.5 ± 0.7 | Not applicable |
| Oil B | 46.0 | 44.0 ± 0.7 | 4.9 |
| Oil C | 25.0 | 24.3 ± 1.3 | 2.5 |
| Oil D | 45.1 | 46.0 ± 0.8 | 11.0 |

Figure 7:
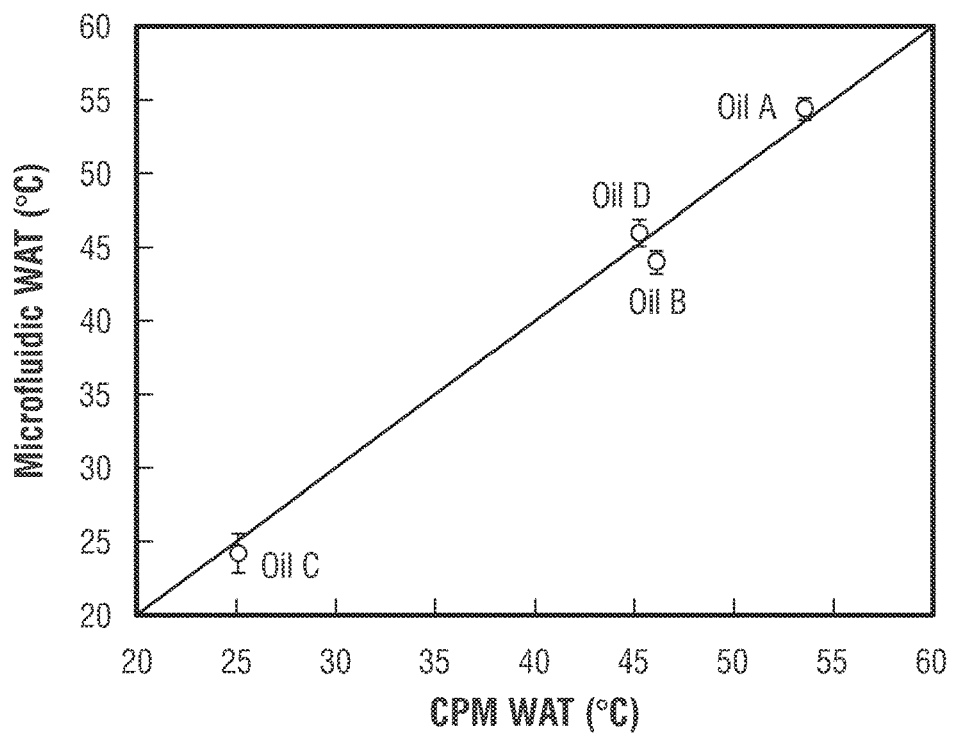
FIG. 7 is a comparison of WAT measurements made according to embodiments of methods for determining the WAT of the oil using microfluidic techniques and WAT measurements made using other techniques.

Procedures followed were the same for all the oil samples. The results from the microfluidic measurements are compared to CPM measured data in FIG. 7. The error bars represent the standard deviation of two separate runs. The microfluidic measurements were repeatable and show excellent agreement with the CPM measured data. The WATs of Oils C and D were unknown prior to the microfluidic test and the WAT of these samples was only measured by CPM after the microfluidic runs. In the case of Oil D, the initial CPM measurement reported was considerably lower (28° C.) than the microfluidic measurement. The sample was retested and the operator detected a small amount of wax crystals at 45.1° C. which demonstrates the operator dependence of the CPM technique. Determination of the WAT from CPM images is also subject to interpretation and requires experience. However, microfluidic measurements are based solely on a pressure variation parameter that is easily measurable with an automated detection process. The close agreement of the microfluidic measurements with the CPM results shows the validity of the microfluidic method as a WAT measurement tool.

One major limitation of the CPM method is the detection limit of wax crystals at wax appearance temperature. Optical detection is not feasible when the crystal size is smaller than 2 microns even if crystals are present in large quantity in the sample. Since the microfluidic technique does not rely on optical detection, it can be used to determine the WAT of samples containing crystals smaller than 2 microns.

In one aspect, a temperature-controlled microfluidic channel with a pressure sensor and a hydrocarbon fluid injector may be located in a tool located in a wellbore. In this manner, a hydrocarbon fluid obtained from an earth formation may be tested for its WAT downhole. The hydrocarbon fluid injector may be a syringe or any other injecting device. Data from the tool may be analyzed downhole or sent uphole. The temperature controller may be located uphole, downhole, or both.

In another aspect, the temperature-controlled microfluidic channel with a pressure sensor and hydrocarbon fluid injector may be located uphole. A hydrocarbon fluid obtained from an earth formation may be brought uphole and tested for its WAT.

In one embodiment a method of determining the WAT of a hydrocarbon fluid sample involves running the hydrocarbon fluid sample through a microfluidic channel at controlled temperatures while sensing a pressure drop across at least a portion of the microfluidic channel, and determining the WAT by finding a first temperature at which the pressure drop across the microfluidic channel caused by a temperature reduction of the hydrocarbon fluid sample does not stabilize over a given time interval. The WAT is established as being at that first temperature or between that first temperature and a second temperature higher than the first temperature where the pressure drop stabilized over time.

Figure 8:
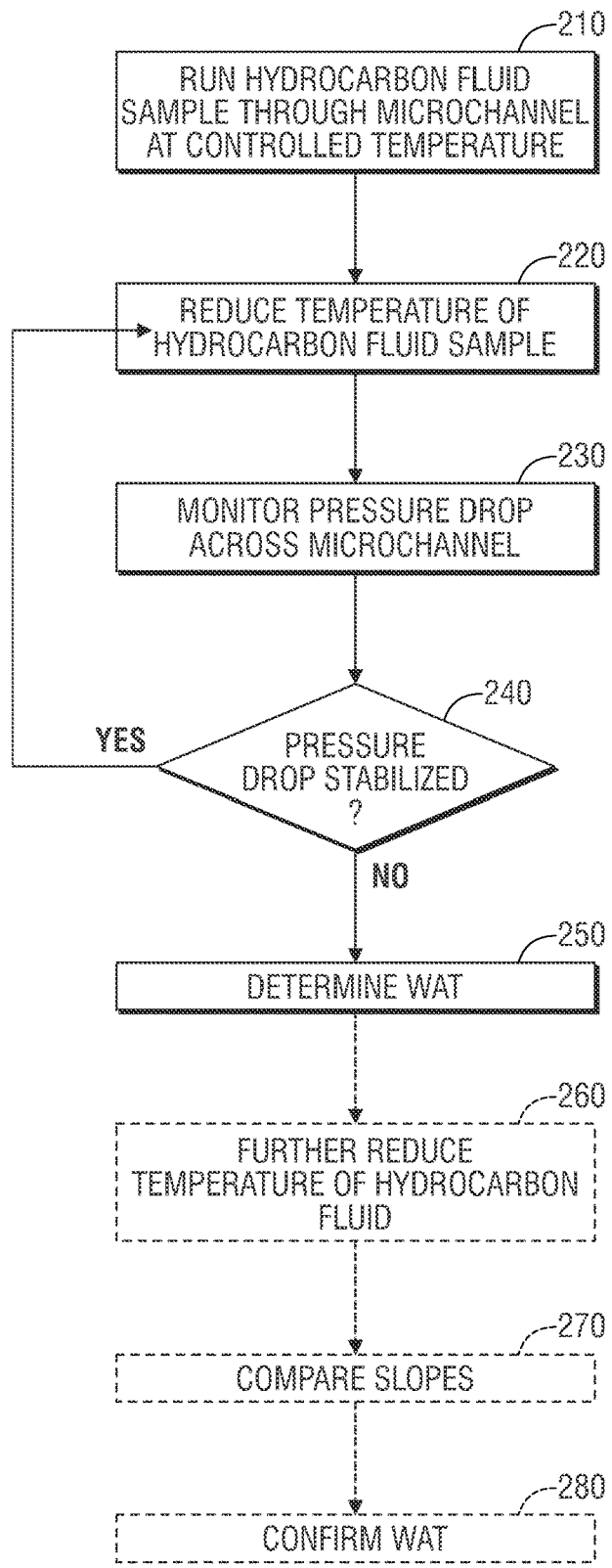
FIG. 8 is a flow chart of a method of making WAT measurements.

FIG. 8 is a flow chart of one embodiment of a method of making WAT measurements. At 210 a hydrocarbon fluid sample is run through a microchannel of a temperature-controlled microfluidic chip at a temperature above the WAT of the hydrocarbon fluid sample. At 220, the temperature of the hydrocarbon fluid sample is reduced to a new temperature. At 230, the pressure (drop) across the microchannel is monitored. At 240, if the pressure (drop) increases and then stabilizes over time, the method returns to 220 where the temperature is further reduced, and the method continues at 230 and 240. If at 240, the pressure (drop) increases and does not stabilize over time, at 250 the WAT is determined as being between the temperature at which the pressure drop no longer stabilizes and a previous higher temperature where the pressure stabilized. If desired, at 260, the temperature of the hydrocarbon fluid sample may be further reduced, and at 270 a comparison may be made between the slope of the pressure (drop) increase at the temperature determined at 250 and that at the new lower temperature. If the slope of the pressure (drop) increase is greater at the further reduced temperature than at the temperature determined at 250, the wax precipitation at the temperature determined at 250 is confirmed at 280.

There have been described and illustrated herein several embodiments of a method and system for determining the WAT of a hydrocarbon fluid sample. While particular embodiments of the invention have been described, it is not intended that the disclosure be limited thereto, as it is intended that it be as broad in scope as the art will allow and that the specification be read likewise. For example, while a single pressure sensor was described for measuring the pressure drop across the microfluidic channel, it will be appreciated that two pressure sensors could be used at the entrance and exit of the microfluidic channel or at the entrance and a point along the channel, or at a point along the channel and the exit, or at two points along the channel, in order to measure a pressure drop. Also, while a syringe and syringe pump were described for causing the hydrocarbon fluid sample to run through the microfluidic channel, it will be appreciated that other pressure-difference inducing tools may be used to cause the hydrocarbon fluid sample to run through the channel, including a vacuum generator. It will therefore be appreciated by those skilled in the art that modifications could be made. Accordingly, all such modifications are intended to be included within the scope of this disclosure as defined in the following claims. In the claims, means-plus-function clauses, if any, are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of determining the wax appearance temperature (WAT) of a hydrocarbon fluid sample, comprising:
   a) running the hydrocarbon fluid sample at a temperature above the WAT through a microfluidic channel;
   b) reducing the temperature of the hydrocarbon fluid sample to a new temperature;
   c) measuring a pressure drop of the hydrocarbon fluid sample across at least a portion of the microfluidic channel at the new temperature over time;
   d) determining, from the measuring of the pressure drop, whether the pressure drop stabilizes over time, and when the pressure drop stabilizes over time, repeating the reducing of the temperature and the measuring of the pressure drop again, and determining whether the pressure drop stabilizes over time and reducing the temperature until determining that the pressure drop no longer stabilizes over time;
   e) establishing the WAT based on a first temperature at which the pressure drop no longer stabilizes over time; and reducing the temperature below the WAT and comparing a pressure drop rise curve at a further reduced temperature with a pressure drop rise curve at the first temperature.

2. A method according to claim 1, further comprising if the pressure drop rise curve at the further reduced temperature has a greater slope than the pressure drop rise curve at the first temperature, confirming that the WAT is a temperature between the first temperature and a previous higher temperature at which the pressure drop stabilizes over time.

3. A method according to claim 1, wherein the reducing is repeated at first regular temperature reductions.

4. A method according to claim 3, further comprising:
   f) increasing the temperature of the hydrocarbon fluid sample above a previous higher temperature at which the pressure drop stabilizes over time;
   g) reducing the temperature of the hydrocarbon fluid sample to an intermediate temperature between the previous higher temperature and the first temperature while measuring a pressure drop of the hydrocarbon fluid sample across at least a portion of the microfluidic channel; and
   h) if the pressure drop stabilizes over time at the intermediate temperature, repeating the reducing the temperature of the hydrocarbon fluid sample to a temperature between the previous higher temperature and the first temperature at second regular temperature reductions smaller than the first regular temperature reductions until the pressure drop no longer stabilizes over time.

5. A method according to claim 4, wherein the increasing the temperature of the hydrocarbon fluid sample above the previous higher temperature comprises causing wax on a wall of the microfluidic channel to dissolve.

6. A method according to claim 1, wherein the temperature of the hydrocarbon fluid sample is controlled by controlling the temperature of the microfluidic channel.

7. A method according to claim 1, wherein the measuring a pressure drop comprises measuring a pressure at an input to the microfluidic channel.

8. A method according to claim 1, wherein the running the hydrocarbon fluid sample through a microfluidic channel comprises running the hydrocarbon fluid sample through the microfluidic channel at a substantially constant flow rate.

9. A method according to claim 1, wherein the running the hydrocarbon fluid sample through a microfluidic channel comprises injecting the hydrocarbon fluid sample via a filter into the microfluidic channel.

10. A method according to claim 1, wherein the WAT is determined to be a temperature between the first temperature and a previous higher temperature at which the pressure drop stabilizes over time.

11. A method of determining the wax appearance temperature (WAT) of a hydrocarbon fluid sample, comprising:
a) running the hydrocarbon fluid sample at a temperature above the WAT through a microfluidic channel;
b) reducing the temperature of the hydrocarbon fluid sample to a new temperature, wherein the temperature of the hydrocarbon fluid sample is controlled by controlling the temperature of the microfluidic channel;
c) measuring a pressure drop of the hydrocarbon fluid sample across at least a portion of the microfluidic channel at the new temperature over time;
d) determining the measuring of the pressure drop, whether the pressure drop stabilizes over time, and when the pressure drop stabilizes over time, repeating the reducing of the temperature and the measuring of the pressure drop again, and determining whether the pressure drop stabilizes over time and reducing the temperature until determining that the pressure drop no longer stabilizes over time; and
e) establishing the WAT based on a first temperature at which the pressure drop does not plateau.

12. A method according to claim 11, further comprising further reducing the temperature below the WAT and comparing a pressure drop rise curve at a further reduced temperature with a pressure drop rise curve at the first temperature.

13. A method according to claim 10, further comprising confirming that the WAT is a temperature between the first temperature and a previous higher temperature at which the pressure drop plateaus when the pressure drop rise curve at the further reduced temperature has a greater slope than the pressure drop rise curve at the first temperature.

14. A method according to claim 11, wherein the reducing is repeated at first regular temperature reductions.

15. A method according to claim 14, further comprising:
f) increasing the temperature of the hydrocarbon fluid sample above a previous higher temperature at which the pressure drop plateaus;
g) reducing the temperature of the hydrocarbon fluid sample to an intermediate temperature between the previous higher temperature and the first temperature while measuring a pressure drop of the hydrocarbon fluid sample across at least a portion of the microfluidic channel; and
h) if the pressure drop plateaus over time at the intermediate temperature, repeating the reducing the temperature of the hydrocarbon fluid sample to a temperature between the previous higher temperature and the first temperature at second regular temperature reductions smaller than the first regular temperature reductions until the pressure drop no longer plateaus over time.

16. A method according to claim 15, wherein the increasing the temperature of the hydrocarbon fluid sample above the previous higher temperature comprises causing wax on a wall of the microfluidic channel to dissolve.

17. A method according to claim 11, wherein the measuring a pressure drop comprises measuring a pressure at an input to the microfluidic channel.

18. A method according to claim 11, wherein the running the hydrocarbon fluid sample through a microfluidic channel comprises running the hydrocarbon fluid sample through the microfluidic channel at a substantially constant flow rate.

19. A method according to claim 11, wherein the running the hydrocarbon fluid sample through a microfluidic channel comprises injecting the hydrocarbon fluid sample via a filter into the microfluidic channel.

20. A method according to claim 11, wherein the WAT is determined to be a temperature between the first temperature and a previous higher temperature at which the pressure drop reaches a plateau.

21. A method of determining the wax appearance temperature (WAT) of a hydrocarbon fluid sample, comprising:
a) running the hydrocarbon fluid sample at a temperature above the WAT through a microfluidic channel;
b) reducing the temperature of the hydrocarbon fluid sample to a new temperature;
c) measuring a pressure drop of the hydrocarbon fluid sample across at least a portion of the microfluidic channel at the new temperature over time, wherein the measuring a pressure drop comprises measuring a pressure at an input to the microfluidic channel;
d) determining the measuring of the pressure drop, whether the pressure drop stabilizes over time, and when the pressure drop stabilizes over time, repeating the reducing of the temperature and the measuring of the pressure drop again, and determining whether the pressure drop stabilizes over time and reducing the temperature until determining that the pressure drop no longer stabilizes over time; and
e) establishing the WAT based on a first temperature at which the pressure drop does not plateau.

* * * * *